(12) United States Patent
Hershberger

(10) Patent No.: US 9,730,616 B2
(45) Date of Patent: Aug. 15, 2017

(54) MECHANICAL AXIS ALIGNMENT USING MRI IMAGING

(75) Inventor: Troy W. Hershberger, Winona Lake, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 1732 days.

(21) Appl. No.: 12/255,945

(22) Filed: Oct. 22, 2008

(65) Prior Publication Data

US 2010/0099977 A1    Apr. 22, 2010

(51) Int. Cl.
*A61B 5/107* (2006.01)
*A61B 5/055* (2006.01)
(Continued)

(52) U.S. Cl.
CPC ............ *A61B 5/1071* (2013.01); *A61B 5/055* (2013.01); *A61B 5/103* (2013.01); *A61B 5/4528* (2013.01);
(Continued)

(58) Field of Classification Search
CPC ............ A61B 17/1742; A61B 17/1739; A61B 5/1071; A61B 5/055; A61B 5/103;
(Continued)

(56) References Cited

U.S. PATENT DOCUMENTS

| | | |
|---|---|---|
| 3,229,372 A | 1/1966 | Quashnock et al. |
| 4,428,571 A * | 1/1984 | Sugarman .................. 5/648 |

(Continued)

FOREIGN PATENT DOCUMENTS

| | | |
|---|---|---|
| FR | 2429582 A1 | 1/1980 |
| WO | WO-9413218 A1 | 6/1994 |

(Continued)

OTHER PUBLICATIONS

International Search Report and Written Opinion mailed Feb. 2, 2010 for PCT/US2009/061434 claiming benefit of U.S. Appl. No. 12/255,945, filed Oct. 22, 2008.

(Continued)

*Primary Examiner* — Bo J Peng (74) *Attorney, Agent, or Firm* — Schwegman Lundberg & Woessner, P.A.

(57) ABSTRACT

A method of imaging a body part includes locating a first, second and third anatomical reference area. The third anatomical reference area is disposed generally between the first and second anatomical reference areas. Furthermore, the method includes positioning a first member of a reference tool relative to the first anatomical reference area, positioning a second member of the reference tool relative to the second anatomical reference area, and a pivotal coupling member relative to the third anatomical reference area. The pivotal coupling member pivotally couples the first and second members of the reference tool. In addition, the method includes imaging a target area of the body part to produce an image. The image includes the target area of the body part and the first and second members. The first member indicates a first axis of the body part, and the second member indicates a second axis of the body part.

23 Claims, 4 Drawing Sheets

(51) Int. Cl.
    *A61B 5/103*     (2006.01)
    *A61B 5/00*     (2006.01)
    *A61B 6/00*     (2006.01)
    *A61B 6/12*     (2006.01)
    *A61B 17/15*     (2006.01)
    *A61B 17/22*     (2006.01)
    *A61B 90/00*     (2016.01)
    *A61B 34/10*     (2016.01)

(52) U.S. Cl.
    CPC . *A61B 6/00* (2013.01); *A61B 6/12* (2013.01); *A61B 17/151* (2013.01); *A61B 2017/22001* (2013.01); *A61B 2034/108* (2016.02); *A61B 2090/067* (2016.02)

(58) Field of Classification Search
    CPC ........... A61B 5/4528; A61B 6/12; A61B 6/00; A61B 2019/508; A61B 2019/467; A61B 2017/22001
    USPC ............................... 606/87, 88, 102; 600/414
    See application file for complete search history.

(56) References Cited

U.S. PATENT DOCUMENTS

| | | | | |
|---|---|---|---|---|
| 4,841,975 A | * | 6/1989 | Woolson | 600/425 |
| 5,007,936 A | * | 4/1991 | Woolson | 128/898 |
| 5,560,728 A | * | 10/1996 | McFadden | 403/53 |
| 5,586,558 A | | 12/1996 | Riley | |
| 5,911,724 A | | 6/1999 | Wehrli | |
| 6,361,506 B1 | | 3/2002 | Saenger et al. | |
| 6,554,837 B1 | | 4/2003 | Hauri et al. | |
| 2003/0069897 A1 | | 4/2003 | Roy et al. | |
| 2003/0074800 A1 | * | 4/2003 | Huang | 33/486 |
| 2005/0015022 A1 | | 1/2005 | Richard et al. | |
| 2005/0027303 A1 | | 2/2005 | Lionberger et al. | |
| 2005/0222573 A1 | | 10/2005 | Branch et al. | |
| 2007/0100258 A1 | | 5/2007 | Shoham et al. | |
| 2007/0185498 A2 | | 8/2007 | Lavallee | |
| 2007/0270680 A1 | | 11/2007 | Sheffer et al. | |
| 2007/0288030 A1 | | 12/2007 | Metzger et al. | |

FOREIGN PATENT DOCUMENTS

| | | |
|---|---|---|
| WO | WO-9901073 A1 | 1/1999 |
| WO | WO-2005099636 A1 | 10/2005 |

OTHER PUBLICATIONS

International Preliminary Report on Patentability and Written Opinion mailed May 5, 2011 for PCT/US2009/061434 claiming benefit of U.S. Appl. No. 12/255,945, filed Oct. 22, 2008.

* cited by examiner

MECHANICAL AXIS ALIGNMENT USING MRI IMAGING

FIELD

The present disclosure relates to magnetic resonance imaging (MRI), computed tomography (CT) or fluoroscopy imaging and, more particularly, relates to mechanical axis alignment using MRI, CT, traditional x-ray scans or fluoroscopy imaging.

BACKGROUND

The statements in this section merely provide background information related to the present disclosure and may not constitute prior art.

Anatomical imaging is often performed prior to surgical procedures. MRI, CT or x-ray is often performed, for instance, before implantation of a prosthetic joint, such as a knee joint. The MRI, CT or x-ray image illustrates the joint, allowing doctors to study the joint prior to surgery. Furthermore, cut guides and/or anatomically matching instrumentation can be generated according to the images. As such, the components of the prosthetic device are more likely to be properly aligned, thereby improving comfort and performance for the patient, decreasing wear of the prosthetic components, and increasing longevity of the components.

In the case of a knee joint, it can be preferable for the reconstructed knee to fulfill a number of anatomical relationships. For instance, the mechanical axis of the leg, which extends from the center of the femoral head (i.e., the acetabulum head of the femur) to the center of the ankle, should pass through the middle of the knee joint. The axis of the femur should be inclined at a predetermined "valgus" angle (e.g., 7 degrees) with the mechanical axis of the leg. Furthermore, the axis of the tibia should be collinear with the mechanical axis of the leg. In addition, the mechanical axis of the leg, the axis of the femur, and the axis of the tibia should lie in a common plane when the leg is straightened. MRI, CT, x-ray or fluoroscopic imaging helps in analyzing the knee joint and to plan for surgery to repair the knee joint in order that the prosthesis achieves these and other relationships. More specifically, the MRI, CT, x-ray or fluoroscopic image can help in planning cut guides and other surgical procedures such that forces in the leg are transferred through the prosthetic components along the mechanical axis of the leg, from the center of the femoral head, through the middle of the knee joint, and to the ankle.

In the case of a knee joint prosthesis, an MRI, CT, x-ray or fluoroscopic image is often taken of multiple areas of the leg. More specifically, an MRI, CT or fluoroscopic image is taken of the knee joint where the prosthetic components will be implanted. Separate images are generated for areas spaced away from the knee joint as well. For instance, images are generated for the hip and/or the ankle in order to obtain a more complete analysis of the leg and to locate the centers of the hip joint and ankle joint.

However, this type of imaging can take a long time and can be a complex process. Specifically, in the case of MRI, the patient is positioned in an MRI system, an MRI imaging coil is placed over the target area of the body, and the MRI image is taken of that target area. Then, the imaging coil is moved to the next target area of the body, and another MRI image is taken. Thus, in the above examples, the knee, hip and ankle are imaged separately. Several MRIs may be necessary, and if the patient moves, the images may be degraded. In addition, in an instance wherein CT, x-ray or fluoroscopy imaging is used, a patient may be subjected to unnecessary radiation as each of the knee, ankle and hip are imaged.

SUMMARY

A method of imaging a body part is disclosed. The method includes locating a first, second and third anatomical reference area of the body part. The third anatomical reference area is disposed generally between the first and second anatomical reference areas. Furthermore, the method includes positioning a first member of a reference tool relative to the first anatomical reference area. The method also includes positioning a second member of the reference tool relative to the second anatomical reference area. Moreover, the method includes positioning a pivotal coupling member relative to the third anatomical reference area. The pivotal coupling member pivotally couples the first and second members of the reference tool. In addition, the method includes imaging a target area of the body part to produce an image. The image includes the target area of the body part and at least a portion of the first and second members. The portion of the first member indicates a first axis of the body part in the image, and the portion of the second member indicates a second axis of the body part in the image.

A reference tool for indicating anatomical features of a body part is also disclosed. The reference tool includes a first member positionable relative to a first anatomical reference area of the body part. The reference tool further includes a second member positionable relative to a second anatomical reference area of the body part. Furthermore, the reference tool includes a pivotable coupling member pivotally coupling the first member and the second member. The pivotable coupling member is locatable relative to a third reference point of the body part disposed generally between the first and second anatomical reference areas. The first member and the second member are detectable on an image of a target area of the body part such that the first member indicates a first axis of the body part in the image and the second member indicates a second axis of the body part in the image.

In another aspect, a method of imaging a knee joint of a leg is disclosed. The method includes locating an approximate center of a femoral head of the leg, locating an approximate center of an ankle joint of the leg, and locating an approximate center of a knee joint of the leg. Furthermore, the method includes positioning a pivotal coupling member over the approximate center of the knee joint of the leg. The pivotal coupling member pivotally couples a first and a second member of a reference tool. Additionally, the method includes pivoting the first member of the reference tool to position the first member over the approximate center of the femoral head and pivoting the second member of the reference tool to position the second member over the approximate center of the ankle joint. Also, the method includes imaging the knee joint to produce an image of the knee joint and at least a portion of the first and second members. The portion of the first member indicates a mechanical axis of the leg in the image, and the portion of the second member indicates a tibial axis of the leg in the image.

In still another aspect, a method of imaging a body part is disclosed that includes locating a first and a second anatomical reference area of the body part. The method also includes positioning a first member of a reference tool relative to the first anatomical reference area. Furthermore, the method includes positioning a second member of the reference tool relative to the second anatomical reference area, wherein the second member is disposed at a positive angle relative to the first member. Moreover, the method includes imaging a target area of the body part to produce an image. The image includes the target area of the body part and at least a portion of the first and second members. The first member indicates a first axis of the body part in the image, and the second member indicates a second axis of the body part in the image.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1:
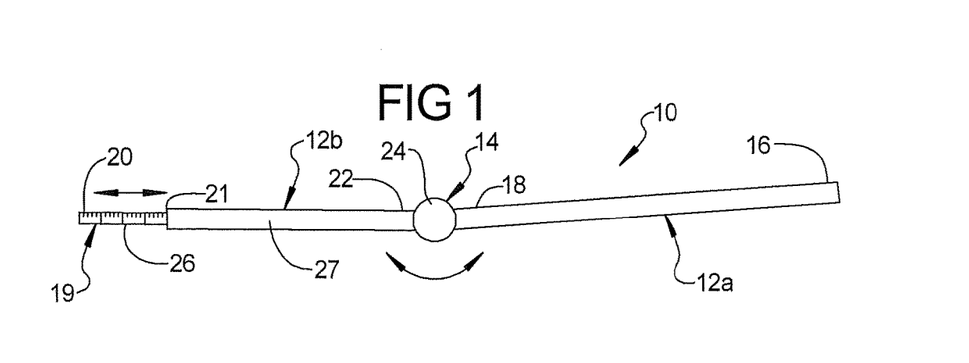
FIG. 1 is a top view of a reference tool according to the present disclosure.

Initially referring to FIG. 1, a reference tool 10 is illustrated. In general, the reference tool 10 includes a first member 12a, a second member 12b, and a pivotable coupling member 14 that is disposed generally between the first and second members 12a, 12b. The pivotable coupling member 14 pivotally couples the first and second members 12a, 12b.

In some embodiments, the pivotable coupling member 14 is a ball joint 24 that pivotally couples the first and second members 12a, 12b. However, it will be appreciated that the pivotable coupling member 14 could be of any suitable type, such as a hinge joint, ball and socket joint, or a flexible coupling member, without departing from the scope of the present disclosure.

Furthermore, in some embodiments, the first member 12a is an elongate member having a substantially straight axis. The first member 12a defines a terminal end 16 and a second end 18 that is coupled to the coupling member 14. Likewise, the second member 12b is an elongate member having a substantially straight axis. The second member 12b defines a terminal end 20 and a second end 22 that is coupled to the coupling member 14. The first and second members 12a, 12b can be made out of a hard, rigid material of any suitable type, such as plastic or carbon fibers.

In some embodiments, at least one of the first and second members 12a, 12b has an adjustable length. For instance, in the embodiment represented in FIG. 1, the second member 12b includes a telescoping member 26 capable of collapsing into a hollow shaft 27. For example, in the depicted embodiment, the telescoping member 26 moveably extends into and out of the hollow shaft 27, thereby varying the distance between the terminal end 20 and the coupling member 14. It will be appreciated that the first member 12a could also include a telescoping member 26 to thereby vary the distance between the terminal end 16 and the coupling member 14. Furthermore, it will be appreciated that the length of the first and/or second member 12a, 12b can be adjustable in any suitable manner; for instance, the first and/or second member 12, 12b could include removably attached extenders and the like. Moreover, both members 12a, 12b may be substantially solid and not adjustable in length.

Additionally, in some embodiments, the reference tool 10 includes a scale 19. In the embodiment illustrated, the scale 19 includes a plurality of evenly spaced demarcations, which could indicate length in inches, millimeters, or any other appropriate unit of measurement. The scale 19 can be used to measure the distance between the terminal end 20 and the center of rotation of the coupling member 14. More specifically, in some embodiments, the sum of the length of the hollow shaft 27 and the radius of the coupling member 14 is known, and the scale 19 is demarcated in order to indicate this sum and the additional distance that the telescoping member 26 is extended out of the hollow shaft 27. Thus, in some embodiments, the user adjusts the position of the telescoping member 26 relative to the shaft 27, and at an intersection of the telescoping member 26 and the shaft 27, the scale 19 indicates the approximate distance between the terminal end 20 and the center of rotation of the coupling member 14.

As will be discussed, the reference tool 10 can be used for indicating features of a body part, such as a knee joint of a leg. In some embodiments, the reference tool 10 is used in conjunction with MRI. In this case, the first member 12a, the second member 12b and the pivotable coupling member 14 are made of a non-magnetic and non-metallic material such that the first member 12a, the second member 12b and the pivotable coupling member 14 are detectable on a MR image of the knee joint. As will be discussed, the reference tool 10 indicates a plurality of axes of the leg for such imaging. It will be appreciated that the reference tool 10 can be used in associated with any other type of imaging process other than MRI (e.g., CT scanning, fluoroscopy, etc.). Furthermore, it will be appreciated that the reference tool 10 can be used for imaging any suitable body part other than a knee joint without departing from the scope of the present disclosure.

Figure 2:
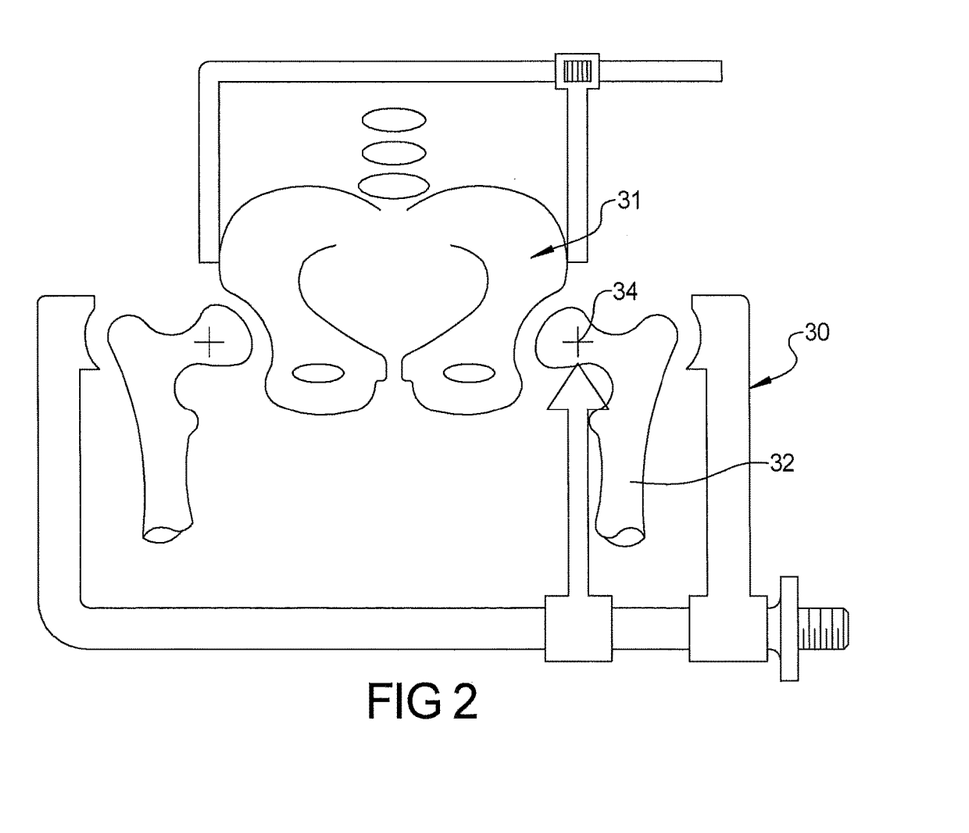
FIG. 2 is a front view of a portion of a skeleton and a locating tool.
Figure 3:
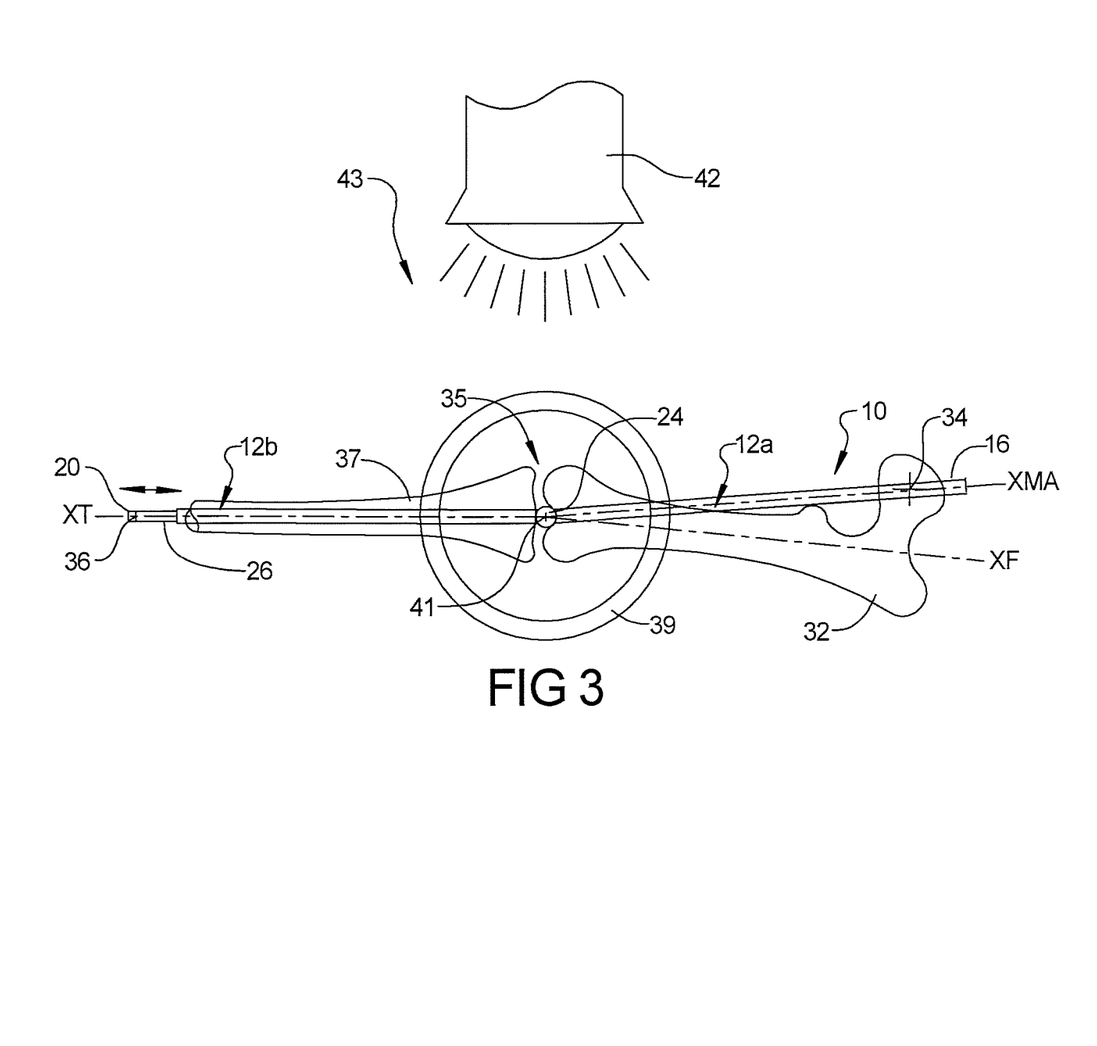
FIG. 3 is a schematic view of the reference tool of FIG. 1 in association with an imaging system according to the present disclosure.

Referring now to FIGS. 2 and 3, a method of imaging a knee joint 35 using the reference tool 10 will be discussed. In some embodiments of the method, an approximate center point 34 of a femoral head (i.e., center of acetabulum head) is initially located as a first anatomical reference area. In some embodiments represented in FIG. 2, the center point 34 of the femoral head is determined using an external jig 30 and known methods. More specifically, the jig 30 is positioned across the patient's pelvis 31 and anatomical measurements are taken using the jig 30. Then, the center point 34 is determined by mathematical calculation based on these anatomical measurements using known ratios. In other words, the width of the pelvis 31 is measured, and then the known ratios are used to estimate the center point 34 of the femoral head. In another embodiment, the center point 34 is determined through fluoroscopic procedures with the jig 30 positioned on the patient. Once the center point 34 is determined, the center point 34 is marked on the patient's skin for future reference.

Next, referring to FIG. 3, a center point 36 of the ankle joint of the patient is located as a second anatomical reference area, and a center point 41 of the knee joint 35 of the patient is located as a third anatomical reference area. In some embodiments, the center point 36 of the ankle joint and the center point 41 of the knee joint 35 are each located visually and by feeling the corresponding joint. It will be understood that the center point 41 of the knee joint 35 will coincide with the joint line of the knee, and thus by locating the center point 41 of the knee joint 35, the joint line of the knee can also be located. The center points 36, 41 can also be marked on the patient's skin for future reference.

Then, the reference tool 10 is positioned relative to the center points 34, 36, 41 as represented in FIG. 3. More specifically, the terminal end 16 of the first member 12a of the reference tool 10 is positioned generally over the center point 34 of the femoral head, the terminal end 20 of the second member 12b is positioned generally over the center point 36 of the ankle joint, and the coupling member 14 is centered generally over the center point 41 of the knee joint 35. In some alternative embodiments, a reference point (not shown) is indicated on the first member 12a between the terminal end 16 and the coupling member 14 for positioning on the center point 34 of the femoral head, and a similar reference point is indicated on the second member 12b for positioning on the center point 36 of the ankle joint.

The reference tool 10 can be secured to the patient's skin such that the terminal end 16 remains over the center point 34, the terminal end 20 remains over the center point 36, and the coupling member 14 remains over the center point 41. Further, the jig 30 shown in FIG. 2 can remain positioned on the patient during the imaging procedure described below.

Once the reference tool 10 is positioned relative to the center points 34, 36, 41, the scale 19 can be used to measure relative distances. For instance, in the embodiments illustrated, the scale 19 indicates the distance from the center point 36 of the ankle joint and the center point 41 of the knee joint 35. It will be appreciated that this data can be useful for subsequent analysis of the leg and for determining the appropriate knee joint prosthesis. It will also be appreciated that the scale 19 could be included on the first member 12a for measuring the distance between the center point 34 of the femoral head and the center point 41 of the knee joint 35.

Next, the patient is positioned within a MRI system 43 as represented schematically in FIG. 3. More specifically, an imaging coil 39 can be positioned over the knee joint 35 as shown in FIG. 3 for improving the signal-to-noise ratio in the image. Then, an MRI emitter 42 is energized to produce an image 40 of the knee joint 35 (i.e., the target area of the body to be imaged), as shown in FIG. 4.

Figure 4:
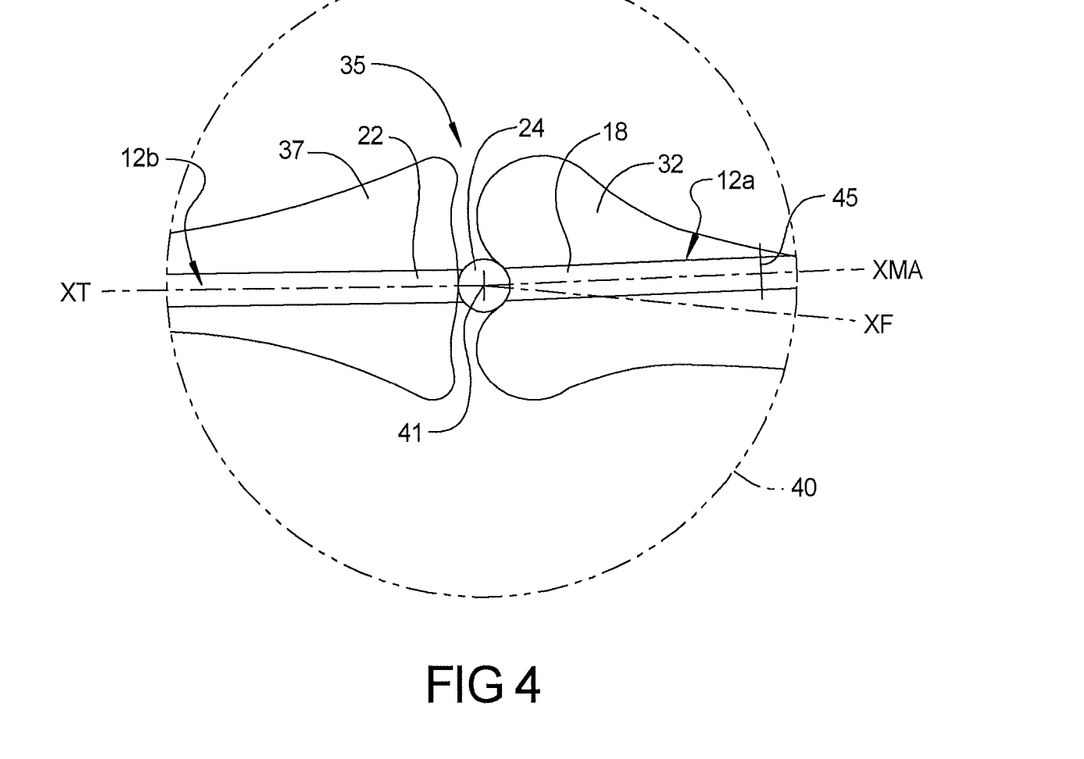
FIG. 4 is a schematic view of an image of a knee joint obtained by the imaging system of FIG. 3.

Referring still to FIG. 4, the resultant image 40 includes the inferior portion of the femur 32 and the superior portion of the tibia 37. Moreover, the second end 18 of the first member 12a and the second end 22 of the second member 12b and the coupling member 14 are also included in the image 40. As shown in FIG. 4, the portion of the first member 12a included in the image 40 indicates a mechanical axis XMA of the leg, and the portion of the second member 12b in the image 40 represents the tibial axis XT of the leg. In some embodiments, the tibial axis XT is determined according to the image of the tibia 37 itself since the tibia 37 is typically straight. The femoral axis XF can also be obtained from the image 40 according to the image of the femur 32.

Thus, the image 40 is substantially localized over the knee joint 35 and excludes the center point 34 of the femoral head and the center point 36 of the ankle joint. This image 40 can be produced in a relatively short amount of time. However, because the mechanical axis XMA, tibial axis XT, and femoral axis XF are included in the image 40 along with the bone anatomy of the patient, the image 40 provides a greater amount of information about the leg than imaging methods of the prior art.

The image 40 can be used for generating one or more custom cut guides for surgically cutting the leg along a cutting direction 45. In some embodiments, the cutting direction 45 is substantially perpendicular to the mechanical axis XMA of the leg as shown in FIG. 4. The custom cut guides can be generated to align one or more knee cuts (and thus the prosthetic components) with the mechanical axis XMA of the leg and not just the bone anatomic alignment. A knee alignment guide, such as the knee alignment guide disclosed in U.S. Patent Publication No. 2007/0288030, which is hereby incorporated by reference in its entirety, can also be generated using the image 40 and imaging method described herein. As such, the prosthetic component can be implanted in an improved manner.

In other embodiments, the reference tool 10 includes a first member 12a and a second member 12b substantially similar to the embodiments discussed above; however, the first and second members 12a, 12b are free from each other and are not attached. Thus, during use, the terminal end 16 of the first member 12a is positioned generally over the center point 34 of the femoral head and the opposite end of the first member 12a is positioned generally over the center point 41 of the knee joint 35. Likewise, the terminal end 20 of the second member 12b is positioned generally over the center point 36 of the ankle joint, and the opposite end of the second member 12b is positioned generally over the center point 41 of the knee joint 35. Then, the medical professional performs imaging the imaging steps discussed above.

Figure 5:
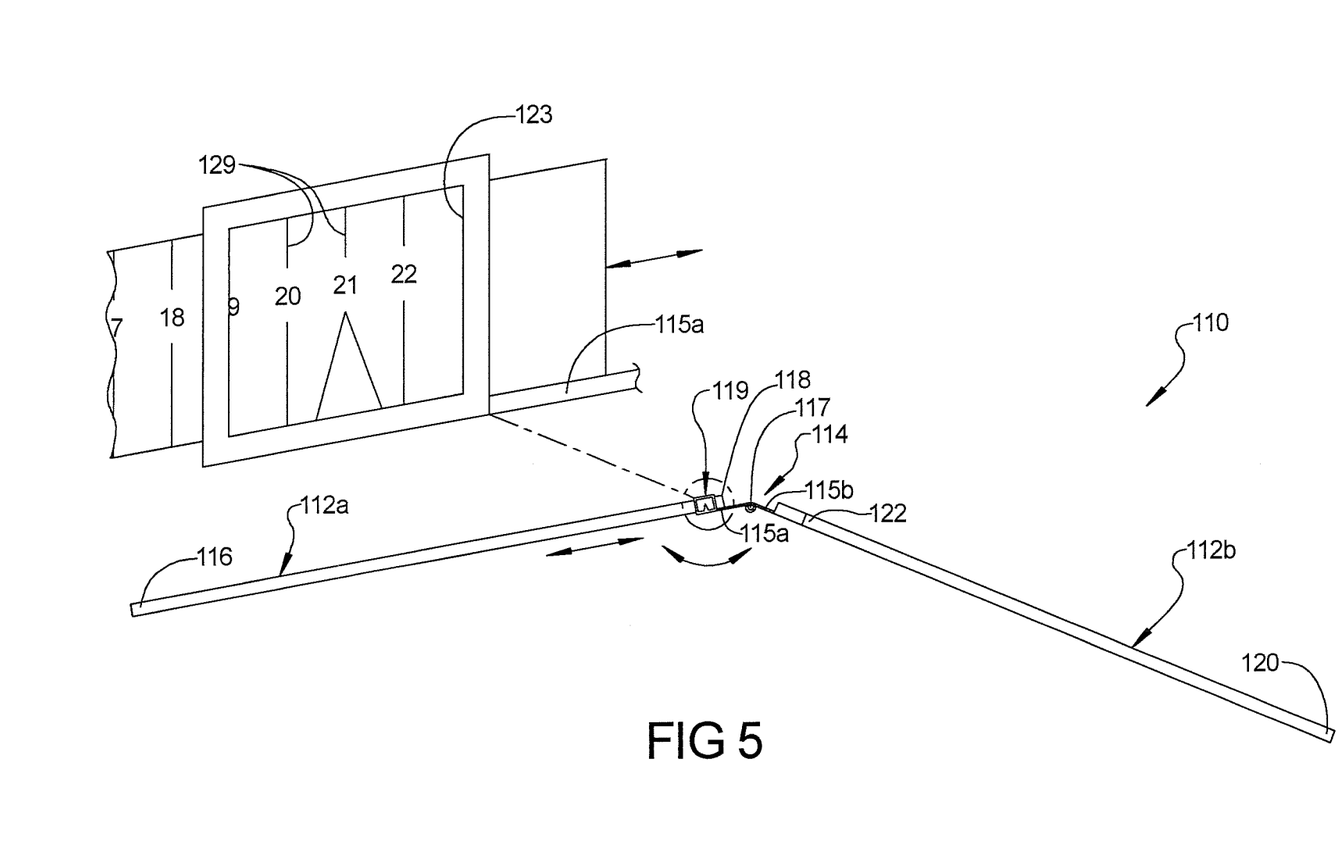
FIG. 5 is a top view of a reference tool according to various other embodiments of the present disclosure.

Referring now to FIG. 5, a reference tool 110 according to various other embodiments of the present disclosure is illustrated. It will be appreciated that components of the reference tool 110 that are similar to those of the embodiment of FIG. 1 are indicated with similar reference numerals, increased by 100.

The reference tool 110 includes a first member 112a and a second member 112b that is pivotally coupled by a coupling member 114. In some embodiments, the coupling member 114 is a hinge having a first portion 115a, and a second portion 115b rotationally coupled by a pin 117. In some embodiments, the first portion 115a is tubular. The first member 112a defines a terminal end 116 and a second end 118 that is slidably received by the first portion 115a of the coupling member 114. The second member 112b defines a terminal end 120 and a second end 122 that, in some embodiments, is fixedly coupled to the second portion 115b of the coupling member 114.

Furthermore, the first portion 115a of the coupling member 114 includes a scale, generally indicated at 119. In some embodiments, the scale 119 includes a window 123 with an indicator 125 in the first portion 115a and a plurality of spaced demarcations 129 included on the first member 112a. As the first member 112a slides relative to the first portion 115a, the indicator 125 indicates the demarcation 129 that corresponds to the distance between the terminal end 116 and the center of rotation of the coupling member 114. Thus, the scale 119 can be used to quickly determine the distance between the center point 34 of the femoral head and the center 41 of the knee joint 35 as described above with respect to the embodiment of FIG. 1. It will also be appreciated that the second member 112b could also include a scale 119 for measuring the distance between the center point 36 of the ankle joint and the center point 41 of the knee joint 35.

In summary, the reference tool 10, 110 and the imaging method disclosed above allow for imaging that is highly effective and accurate. The imaging method can be completed in a relatively short amount of time. Furthermore, the image 40 allows the knee joint 35 to be analyzed based on the anatomic alignment (i.e., the anatomy of the knee joint 35), and the reference tool 10 indicates the axes of the leg in the same image 40 for more accurate analysis of the knee joint 35. Accordingly, the prosthesis can be implanted more accurately and/or custom implant positioning guide can be made to orientate the implant relative to a desired axis.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the steps of the method described herein can be changed without departing from the scope of the present disclosure.

What is claimed is:

1. A method of imaging a knee joint of a leg before surgery comprising:
    locating an approximate center of a femoral head of the leg;
    locating an approximate center of an ankle joint of the leg;
    locating an approximate center of a knee joint of the leg;
    positioning a pivotal coupling member over the approximate center of the knee joint of the leg, the pivotal coupling member pivotally coupling a first and a second member of a reference tool;
    pivoting the first member of the reference tool relative to the second member to position the first member over the approximate center of the femoral head;
    pivoting the second member of the reference tool relative to the first member to position the second member over the approximate center of the ankle joint; and
    imaging the knee joint to produce an image of the knee joint and at least a portion of the first and second members, the at least a portion of the first member indicating a mechanical axis of the leg in the image, and the at least a portion of the second member indicating a tibial axis of the leg in the image, and wherein the image includes the knee joint and excludes the femoral head and the ankle joint.

2. The method of claim 1, further comprising identifying a joint line of the leg.

3. The method of claim 1, further comprising positioning a distal end of the first member of the reference tool over the approximate center of the femoral head.

4. The method of claim 1, further comprising positioning a distal end of the second member over the approximate center of the ankle joint.

5. The method of claim 1, further comprising extending a length of at least one of the first and second members to at least one of position the first member over the approximate center of the femoral head and position the second member over the approximate center of the ankle joint.

6. The method of claim 5, wherein extending the length of the at least one of the first and second members includes moving an indicator of the reference tool relative to a plurality of demarcations on the reference tool, and further comprising determining which of the plurality of demarcations that the indicator is indicating to at least one of measure an approximate distance between the center of the knee joint and the center of the ankle joint and measure an approximate distance between the center of the knee joint and the center of the femoral head.

7. The method of claim 1, wherein the pivotal coupling member includes a ball joint.

8. The method of claim 1, wherein locating an approximate center of the femoral head includes positioning an external jig over a pelvis, imaging the pelvis and the external jig to produce an image that shows at least a portion of the pelvis and at least a portion of the external jig, and determining the approximate center of the femoral head from the image.

9. The method of claim 1, further comprising removably attaching the reference tool to a section of skin of the leg with the pivotal coupling member positioned over the approximate center of the knee joint, the first member over the approximate center of the femoral head, and the second member over the approximate center of the ankle joint.

10. The method of claim 1, further comprising marking a section of skin of the leg to indicate at least one of the approximate center of the ankle joint and the approximate center of the knee joint.

11. The method of claim 1, wherein the reference tool is made of a non-metallic material.

12. The method of claim 1, further comprising generating a cutting guide that is customized according to the mechanical axis of the leg in the image, the cutting guide operable to guide cutting of the knee joint.

13. The method of claim 12, wherein generating the cutting guide includes generating a cutting guide that is operable to guide cutting of the knee joint substantially perpendicular to the mechanical axis of the leg.

14. A method of imaging a knee joint of a leg before surgery comprising:
    positioning a reference tool detectable by imaging over a knee joint of a leg of a patient;
    positioning a pivotal coupling member of the reference tool about a center of the knee joint;
    pivoting a first member of the reference tool about the pivotal coupling member relative to a second member to position a distal end of the first member over a center of a femoral head of the leg;
    pivoting the second member of the reference tool about the pivotal coupling member relative to the first member to position the second member over a center of an ankle joint of the leg;
    obtaining an image of the knee joint with a portion of the reference tool, wherein the image includes the knee joint and excludes the femoral head and the ankle joint; and
    determining a mechanical axis of the leg from the image.

15. The method of claim 14, further comprising telescoping the first member toward the femoral head to position the distal end of the first member over the center of the femoral head of the leg.

16. The method of claim 14, further comprising telescoping the second member toward the ankle joint to position the second member over the center of the ankle joint of the leg.

17. The method of claim 14, further comprising measuring a distance between the center of the ankle joint and the center of the knee joint using a scale extending from the second member.

18. The method of claim 14, further comprising determining a tibial axis of the leg from the image of the knee joint.

19. The method of claim 14, further comprising determining the center of the femoral head using an external jig by positioning the external jig across a pelvis, obtaining at least one measurement of the pelvis using the jig, and calculating the center of the femoral head based on the at least one measurement of the pelvis and a known ratio.

20. A method of imaging a knee joint of a leg before surgery comprising:
   determining a center of a femoral head of a leg of a patient;
   determining a center of the ankle joint of the leg;
   determining a center of the knee joint of the leg;
   positioning a pivotal coupling member of a reference tool about the center of the knee joint, the pivotal coupling member pivotally coupling a first member and a second member of the reference tool;
   pivoting the first member relative to the second member to position a distal end of the first member over the center of the femoral head and to position a distal end of the second member over the center of the ankle joint;
   obtaining an image of the knee joint showing the pivotal coupling member and at least portions of the first and second members extending from the pivotal coupling member;
   determining a mechanical axis of the leg from the image of first member; and
   determining a tibial axis from the image of the second member.

21. The method of claim 20, wherein the image includes the knee joint and excludes the femoral head and the ankle joint.

22. The method of claim 20, further comprising telescopically extending the second member to position the distal end of the second member over the center of the ankle joint.

23. The method of claim 20, further comprising telescopically extending the first member to position the distal end of the first member over the center of the femoral head.

* * * * *